United States Patent [19]

Kaplan et al.

[11] Patent Number: 5,019,093
[45] Date of Patent: May 28, 1991

[54] BRAIDED SUTURE

[75] Inventors: Donald S. Kaplan, Weston; Matthew E. Hermes, Easton, both of Conn.

[73] Assignee: United States Surgical Corporation, Norwalk, Conn.

[21] Appl. No.: 491,215

[22] Filed: Mar. 9, 1990

Related U.S. Application Data

[63] Continuation of Ser. No. 344,745, Apr. 28, 1989, which is a continuation-in-part of Ser. No. 227,699, Aug. 3, 1988, abandoned, which is a continuation-in-part of Ser. No. 89,732, Aug. 26, 1987, abandoned.

[51] Int. Cl.⁵ .............................................. A61B 17/06
[52] U.S. Cl. ..................................... 606/228; 606/230
[58] Field of Search ............... 606/228, 229, 230, 231; 139/387, 388; 87/6, 8, 9

[56] References Cited

U.S. PATENT DOCUMENTS

| 3,125,095 | 3/1964 | Kaufman et al. | 128/335.5 |
|---|---|---|---|
| 3,187,752 | 6/1965 | Glick | 128/335.5 |
| 3,297,033 | 1/1967 | Schmitt | 128/335.5 |
| 3,359,983 | 12/1967 | Northey | 128/335.5 |
| 3,371,069 | 2/1968 | Miyamae et al. | 128/335.5 |
| 3,565,077 | 2/1971 | Glick | 128/335.5 |
| 3,772,420 | 11/1973 | Glick et al. | 128/335.5 |
| 3,949,755 | 4/1976 | Vauquios | 128/335.5 |
| 3,949,756 | 4/1976 | Aee | 128/339 |
| 4,014,973 | 3/1977 | Thompson | 128/335.5 |
| 4,024,871 | 5/1977 | Stephenson | 128/335.5 |
| 4,043,344 | 8/1977 | Landi et al. | 606/230 |
| 4,047,533 | 9/1977 | Perciaccante et al. | 606/230 |
| 4,201,216 | 5/1980 | Mattei | 128/335.5 |
| 4,204,542 | 5/1980 | Bokros et al. | 128/335.5 |
| 4,321,038 | 3/1982 | Porteous | 128/335.5 |
| 4,362,162 | 12/1982 | Nakajima et al. | 128/334 R |
| 4,546,769 | 10/1985 | Planck et al. | 606/231 |
| 4,621,638 | 11/1986 | Silvestrini | 128/335.5 |
| 4,792,336 | 12/1988 | Hlavacek et al. | 128/335.5 |

Primary Examiner—Randall L. Green
Assistant Examiner—Gary Jackson
Attorney, Agent, or Firm—Thomas R. Bremer; Peter G. Dilworth; Rocco S. Barrese

[57] ABSTRACT

A braided suture is provided which exhibits perceptibly enhanced flexibility and hand as well as reduced chatter and drag compared to these same characteristics in a suture possessing substantially the same overall denier but possessing significantly fewer sheath yarns and denier of individual filaments than the braided suture herein.

48 Claims, 5 Drawing Sheets

BRAIDED SUTURE

CROSS REFERENCE TO RELATED APPLICATION

This application is a continuation of commonly assigned, copending U.S. Pat. application Ser. No. 344,745, filed Apr. 28, 1989 as a continuation-in-part of commonly assigned, U.S. Pat. application Ser. No. 227,699, filed Aug. 3, 1988 now abandoned, as a continuation-in-part of commonly assigned, U.S. Pat. application Ser. No. 89,732, filed Aug. 26, 1987, now abandoned.

BACKGROUND OF THE INVENTION

This invention relates to a braided suture of improved construction.

Sutures intended for the repair of body tissues must meet certain requirements: they must be substantially non-toxic, capable of being readily sterilized, they must have good tensile strength and have acceptable knot-tying and knot-holding characteristics and if the sutures are of the absorbable or biodegradable variety, the absorption or biodegradation of the suture must be closely controlled.

Sutures have been constructed from a wide variety of materials including surgical gut, silk, cotton, a polyolefin such as polypropylene, polyamide, polyglycolic acid, polyesters such as polyethylene terephthalate and glycolide-lactide copolymer, etc. Although the optimum structure of a suture is that of a monofilament, since certain materials of construction would provide a stiff monofilament suture lacking acceptable knot-tying and knot-holding properties, sutures manufactured from such materials are preferably provided as braided structures. Thus, for example, sutures manufactured from silk, polyamide, polyester and bio-absorbable glycolide-lactide copolymer are usually provided as multifilament braids. Commercial examples of such sutures include DEXON (Davis & Geck, Inc.,) and VICRYL (Ethicon, Inc.).

Currently available braided suture products are acceptable in terms of their knot-tying and knot-holding properties. However, as removed from the package, they tend to be stiff and wiry and retain a "set" or "memory" such that at the time of use, it is usually necessary for the surgeon or assistant personnel to flex and stretch the suture to make it more readily handible. Furthermore, the surfaces of known sutures are perceptibly rough. Thus, if one passes one's hand or fingers along the braid, surface irregularities will be readily detected. The result of this rough surface is that the suture will exhibit drag or chatter as it is drawn through tissue, characteristics which militate against smooth, neat, accurately placed wound approximation so necessary to excellence in surgical practice.

In the case of one braided suture now on the market, due to the necessity of having to meet fiber strength requirements while at the same time retaining acceptable knot-tying and knot-holding properties, the suture is constructed from a greater amount of fiber and consequently is of larger diameter than the accepted industry standard.

It is an object of this invention to provide a braided suture of improved characteristics, specifically one exhibiting greater flexibility, better hand and less chatter and drag, than braided sutures of known construction.

It is a particular object of the invention to provide a braided suture possessing a greater number of sheath yarns, a finer denier for the individual filaments comprising an individual sheath yarn and a greater pick count for a suture of any given overall denier (crossovers per linear inch).

It is still another object of the invention to provide a braided absorbable suture possessing the aforesaid improved characteristics.

SUMMARY OF THE INVENTION

By way of satisfying the foregoing objects as well as other objects of the invention, there is provided in accordance with this invention a braided suture of improved construction possessing a significantly greater number of sheath yarns for a given overall denier, said sheath yarns being fabricated from individual filaments of finer denier than filaments which are typical of known types of braided suture, said improved suture exhibiting perceptibly improved flexibility and hand and reduced chatter and drag compared with braided sutures of known construction.

More particularly, in accordance with this invention, a braided suture of improved construction is provided wherein for a given range of overall suture denier, the range of pick count, number of sheath yarns and denier of individual filaments comprising a sheath yarn are related to each other as follows:

| Overall Suture Denier | Pick Count | Number of Sheath Yarns | Denier of Individual Filaments |
|---|---|---|---|
| from about 50 to about 125 | from about 50 to about 100 | from about 4 to about 16 | from about 0.2 to about 1.8 |
| greater than about 125 to about 200 | from about 50 to about 100 | from about 4 to about 16 | from about 0.2 to about 1.8 |
| greater than about 200 to about 300 | from about 50 to about 100 | from about 4 to about 16 | from about 0.2 to about 1.8 |
| greater than about 300 to about 500 | from about 50 to about 100 | from about 10 to about 20 | from about 0.2 to about 6.0 |
| greater than about 500 to about 800 | from about 50 to about 100 | from about 14 to about 20 | from about 0.2 to about 6.0 |
| greater than about 800 to about 1200 | from about 50 to about 100 | from about 16 to about 32 | from about 0.2 to about 6.0 |
| greater than about 1200 to about 2000 | from about 50 to about 100 | from about 20 to about 36 | from about 0.2 to about 6.0 |
| greater than about 2000 to about 4000 | from about 50 to about 100 | from about 20 to about 36 | from about 0.2 to about 6.0 |

As a result of its possessing a greater pick count and/or a greater number of sheath yarns for a suture of given overall denier and in some cases, a finer denier for the individual filaments making up a sheath yarn, the braided suture of the present invention exhibits far fewer surface discontinuities thereby providing a suture which is considerably smoother than braided sutures of known construction.

The term "suture" is intended to embrace both the non-absorbable as well as the bio-absorbable varieties.

The term "braid" or "braided" as applied to the suture of this invention refers to an arrangement of discrete units, or bundles, denominated "sheath yarns", made up of individual filaments with individual sheath yarns interlocking or interlacing each other in a regular criss-cross pattern.

The term "pick count" refers to the number of crossovers of sheath yarns per linear inch of suture and, together with the overall denier of the suture, the denier of the individual filaments constituting a sheath yarn and the number of sheath yarns employed, defines the principal construction characteristics of the braided suture herein.

The braided suture of this invention can optionally possess, in addition to the braided structure itself, a core component around which the braid is constructed. In the case of this embodiment, it is preferred that the core constitute a larger proportion of overall suture denier than the core component of a known braided suture

BRIEF DESCRIPTION OF THE ACCOMPANYING FIGURES

The accompanying figures are photomicrographs of cross-sectional and linear views of braided sutures both within (FIGS. 3, 4 and 7 to 10) and outside (FIGS. 1, 2, 5 and 6) the scope of this invention, the latter being presented for comparison purposes.

DESCRIPTION OF THE PREFERRED EMBODIMENTS

Figure 1:
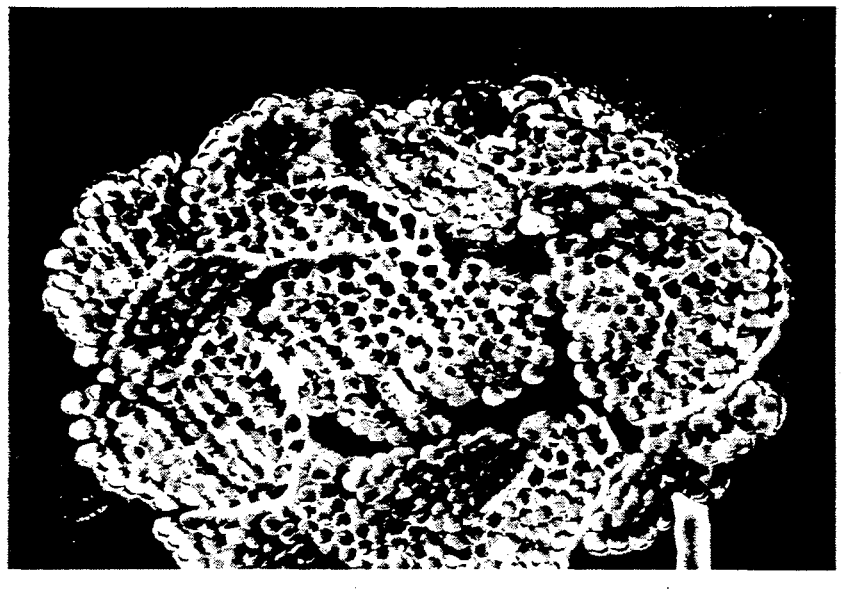

In a preferred embodiment, the braided suture of the present invention is fabricated from a bio-absorbable or biodegradable resin such as one derived from polyglycolic acid, glycolide, lactic acid, lactide, dioxanone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Patent No. 779,291; D. K. Gilding et al., "Biodegradable polymers for use in surgery—polyglycolic/poly(lactic acid) homo- and co-polymers: 1, Polymer, Volume 20, pages 1459-1464 (1979), and D. F. Williams (ed.), Biocompatibility of Clinical Implant Materials, Vol. II, ch. 9: "Biodegradable Polymers" (1981).

The defining characteristics of the braided suture of this invention, apart from the material of its construction, are:

(1) overall suture denier;
(2) the pattern of the interlocking yarns expressed as the pick count, which is to say, the number of crossovers of individual sheath yarns per linear inch of suture;
(3) the number of sheath yarns comprising the braid;
(4) the denier of the individual filaments comprising each sheath yarn; and,
(5) the denier of the core, where present.

(1) Overall Denier of the Suture

The overall denier of the braided suture can vary from about 50 to about 4000. Within this range, the ranges of overall denier for particular sutures are: from about 50 to about 125 denier; from above about 125 to about 200 denier; from above about 200 to about 300 denier; from above about 300 to about 500 denier; from above about 500 to about 800 denier; from above about 800 to about 1500 denier; from above about 1500 to about 2000 denier; and, from above about 2000 to about 3600 denier.

(2) Pattern of the Interlocking Sheath Yarns (Pick Count)

For a suture of any range of overall denier, pick count can vary from about 50 to about 100 crossovers/inch with about 55-80 crossovers/inch being preferred. For sutures constructed within any range of overall denier, as larger numbers of sheath yarns are employed, the pick-count for acceptable sutures will also increase within the above ranges.

For a suture of a particular range of denier and number of sheath yarns, pick count is advantageously established to achieve a balance in the properties desired. In general, with increasing pick count, surface roughness of the suture tends to increase and with decreasing pick count, the ability of the external braided sheath to contain the core (if present) tends to decrease even reaching the point where the braid may become so loose as to result in the core protruding therethrough.

For sutures of any specific denier range and number of sheath yarns, it is preferable to have as low a pick count as possible in order to achieve optimum surface smoothness, consistent, of course, with the need to provide a compact braid which prevents the core (if present) from protruding through the exterior sheath yarn structure.

(3) The Number of Sheath Yarns

The number of sheath yarns bears some relation to overall suture denier, the number generally increasing with the weight of the suture. Thus, across the range of suture weight (denier) indicated above, the braided suture of this invention can be constructed with from about 4 up to as many as about 36 individual sheath yarns constructed from individual filaments having the deniers discussed below.

Table I below sets forth broad and preferred ranges for the numbers of sheath yarns which are suitable for the construction of braided sutures of various ranges of overall denier. The pick counts of the sutures vary from about 50 to about 100 and deniers of individual filaments vary from about 0.2 to about 6.0 for the broad range of number of sheath yarns and the pick counts vary from about 55 to about 80 and the deniers of individual filaments vary from about 0.8 to about 3.0, and advantageously from about 0.8 to about 1.4, for the preferred range of number of sheath yarns.

TABLE I

| Sheath Yarns Related to Suture Denier | | | |
|---|---|---|---|
| Overall Suture Denier | Suture Size | Number of Sheath Yarns (Broad Range) | Number of Sheath Yarns (Preferred Range) |
| 50 to about 125 | 7/0,8/0 | 4-16 | 6-14 |
| greater than about 125 to about 200 | 6/0 | 4-16 | 6-14 |
| greater than about 200 to about 300 | 5/0 | 4-16 | 6-14 |
| greater than about 300 to about 500 | 4/0 | 10-20 | 12-14 |
| greater than about 500 to about 800 | 3/0 | 14-20 | 14-18 |
| greater than about 800 to about 1200 | 2/0 | 18-32 | 20-30 |
| greater than about 1200 to about 2000 | 0 | 20-36 | 24-34 |
| greater than about 2000 to about 4000 | 1,2 | 20-36 | 24-34 |

While the sheath yarns need not be twisted, it is generally preferred that they be provided with a twist so as to minimize snagging during braid construction.

(4) Individual Filament Denier

The individual filaments comprising each sheath yarn can vary in weight from about 0.2 to about 6.0 denier, preferably from about 0.8 to about 3.0 denier and more preferably from about 0.8 to about 1.4 denier. The number of such filaments present in a particular sheath yarn will depend on the overall denier of the suture as well as the number of sheath yarns utilized in the construction of the suture. Table II sets forth some typical numbers of filaments per sheath yarn for both the broad and preferred ranges of filament weight:

TABLE II

| Number of Filaments per Sheath Yarn | | |
|---|---|---|
| approximate minimum | approximate maximum | Filament Denier |
| 45 | 450 | 0.2 |
| 15 | 150 | 0.5 |
| 5 | 50 | 1.5 |
| 3 | 40 | 1.8 |
| 1 | 15 | 6.0 |

(5) Core (Optional)

For all but the lowest range of overall denier, the braided suture herein can optionally be constructed around a filamentous core which itself can be braided or which can be provided in some other configuration such as a twist, ply, cable, etc. The filament(s) comprising the core need not be as fine as those comprising the sheath yarns. It is particularly advantageous for sutures of heavier denier to possess a core. Where a core is provided, it is generally preferred that it possess a weight which is significantly greater than that of a core of a known suture of equivalent overall denier.

Table III below provides some typical core deniers for sutures of various deniers.

TABLE III

| Core Denier Related to Suture Denier | | | |
|---|---|---|---|
| Overall Suture Denier | Suture Size | Denier of Optional Core (Broad Range) | Denier of Optional Core (Preferred Range) |
| from about 50 to about 125 | 8/0, 7/0 | none | none |
| greater than about 125 to about 200 | 6/0 | 20–80 | 25–50 |
| greater than about 200 to about 300 | 5/0 | 30–100 | 50–80 |
| greater than about 300 to about 500 | 4/0 | 80–50 | 80–120 |
| greater than about 500 to about 800 | 3/0 | 150–300 | 180–280 |
| greater than about 800 to about 1200 | 2/0 | 250–700 | 350–650 |
| greater than about 1200 to about 2000 | 0 | 400–1200 | 500–1000 |
| geater than about 2000 to about 4000 | 1,2 | 800–2400 | 1000–2200 |

It can be advantageous to apply one or more coating compositions to the braided suture of this invention to improve such properties as surface lubricity and knot tiedown behavior. A variety of suture coating compositions proposed for either or both purposes is known in the art, e.g., those disclosed in U.S. Pat. No. 4,047,533, the contents of which are incorporated by reference herein.

It is also within the scope of this invention to impregnate the suture with, or otherwise apply thereto, one or more medico-surgically useful substances, e.g.; those which accelerate or beneficially modify the healing process when the suture is applied to a wound or surgical site. So, for example, the braided suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamycin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or several growth promoting factors can be introduced into the suture, e.g., fibroblast growth factor, bone growth factor, epidermal growth factor, platelet derived growth factor, macrophage derived grown factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

In the examples which follow, Comparison Examples 1 to 11 are illustrative of known type sutures while Examples 1 to 12 are illustrative of sutures constructed in accordance with this invention.

COMPARISON EXAMPLES 1–7

The following braided suture configurations are disclosed in U.S. Pat. No. 3,565,077;

| Comparison Example | Overall Suture Denier | Pick Count | Number of Sheath Yarns | Denier of Individual Filaments | Denier of Core |
|---|---|---|---|---|---|
| 1 | 175 | 40 | 6 | 6 | 25 |
| 2 | 300 | 46 | 8 | 6 | 100 |
| 3 | 500 | 40 | 8 | 6 | 100 |
| 4 | 800 | 50 | 12 | 6 | 200 |
| 5 | 1200 | 50 | 16 | 6 | 400 |
| 6 | 1500 | 50 | 12 | 6 | 600 |
| 7 | 2000 | 40 | 16 | 6 | 800 |

Sutures possessing approximately these configurations are relatively inflexible, rough-surfaced and exhibit a relatively high level of chatter and drag.

COMPARISON EXAMPLES 8–11

The following braided suture configurations are those of four commercially available sutures:

| Comparison Example | Overall Suture Denier | Suture Size | Pick Count | Number of Sheath Yarns | Denier of Individual Filaments | Denier of Core |
|---|---|---|---|---|---|---|
| 8 | 259 | 5/0 | 47 | 8 | 2.1 | 29 |

| Comparison Example | Overall Suture Denier | Suture Size | Pick Count | Number of Sheath Yarns | Denier of Individual Filaments | Denier of Core |
| --- | --- | --- | --- | --- | --- | --- |
| 9 | 698 | 3/0 | 52 | 12 | 2.1 | 55 |
| 10 | 1566 | 0 | 50 | 16 | 2.1 | 252 |
| 11 | 2122 | 1 | 44 | 16 | 2.2 | 330 |

Photomicrographs obtained by scanning electron microscopy (SEM) of the suture of Comparison Example 10 (FIGS. 1 and 2: cross-sectional view at 200× and linear view at 50×, respectively) clearly show the structural details of the suture. The suture braid is made up of relatively few sheath yarns and the circumferential indentations, plainly evident in FIG. 1, cause the braid surface to be relatively rough.

EXAMPLES 1-8

These examples illustrate various size braided sutures constructed in accordance with the present invention.

| Example | Overall Suture Denier | Suture Size | Pick Count | Number of Sheath Yarns | Denier of Individual Filaments | Denier of Core |
| --- | --- | --- | --- | --- | --- | --- |
| 1 | 96 | 7/0 | 82 | 8 | 1.2 | — |
| 2 | 173 | 6/0 | 75 | 12 | 1.2 | 29 |
| 3 | 240 | 5/0 | 65 | 8 | 1.2 | 48 |
| 4 | 389 | 4/0 | 75 | 12 | 1.2 | 101 |
| 5 | 600 | 3/0 | 65 | 16 | 1.2 | 216 |
| 6 | 1080 | 2/0 | 72 | 24 | 1.2 | 504 |
| 7 | 1378 | 0 | 65 | 28 | 1.2 | 706 |
| 8 | 2028 | 1 | 65 | 32 | 1.2 | 1260 |

Comparing the details of construction of the foregoing braided sutures with those of the known braided sutures as set forth in Comparison Examples 1-11, it will be noted that for sutures of comparable overall denier, the suture of this invention possesses a significantly greater pick count and number of sheath yarns and a significantly finer denier for the individual filaments making up a sheath yarn than the equivalent characteristics of the known As a result of their unique construction characteristics, the sutures of this invention exhibit perceptibly improved flexibility and hand and reduced chatter and drag compared with the known sutures of Comparison Examples 1-11.

EXAMPLES 9-12

The following braided sutures were fabricated in accordance with the present invention:

| Example | Overall Suture Denier | Suture Size | Pick Count | Number of Sheath Yarns | Denier of Individual Filaments | Denier of Core |
| --- | --- | --- | --- | --- | --- | --- |
| 9 | 240 | 5/0 | 68 | 8 | 1.2 | 40 |
| 10 | 600 | 3/0 | 71 | 16 | 1.2 | 180 |
| 11 | 1374 | 0 | 67 | 28 | 1.2 | 702 |
| 12 | 2230 | 1 | 57 | 32 | 1.2 | 975 |

In contrast to the suture of Comparison Example 10, supra, SEM photomicrographs of the suture of Example 11 (FIGS. 3 and 4: cross-sectional view at 200× and linear view at 50×, respectively) show a smooth circumferential surface as the result of the increased number of sheath yarns and smaller diameter of individual filaments.

Figure 3:
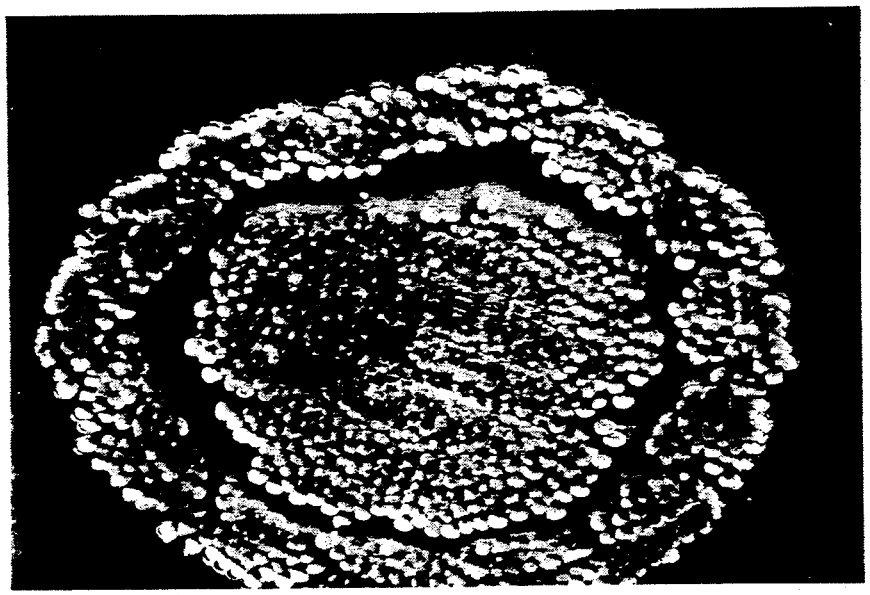

FIG. 1 as compared to FIG. 3 shows the relatively larger core present in the suture of Example 11 as compared to that of Comparison Example 10.

Figure 2:
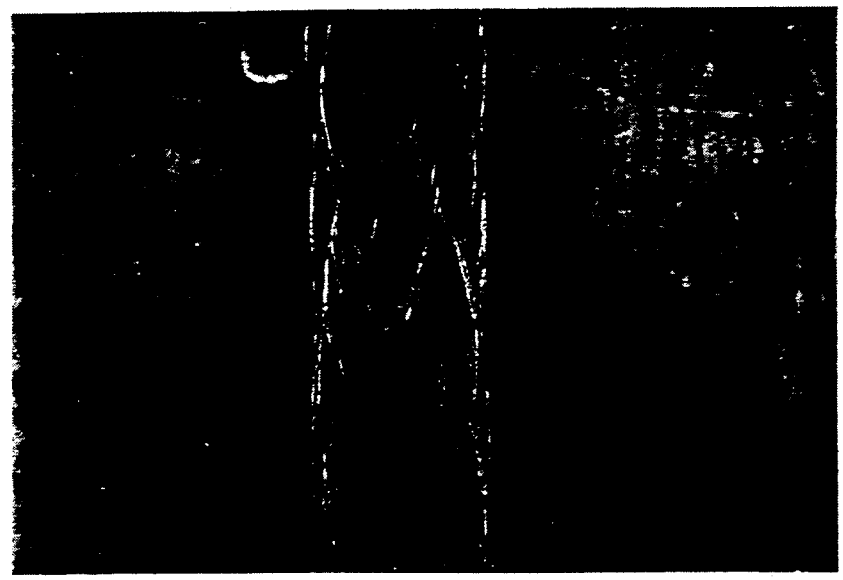
Figure 4:
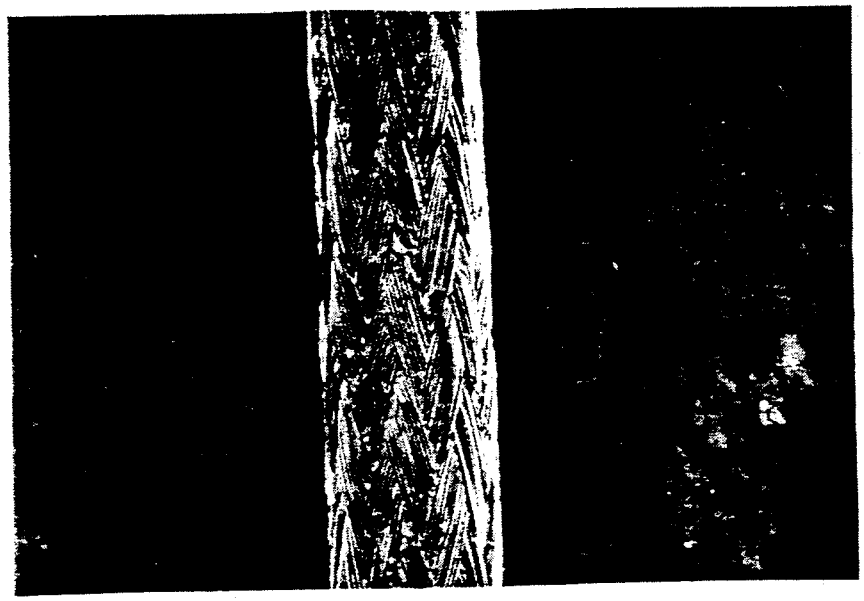

Comparison between FIGS. 2 and 4 shows the increased number of picks (crossovers/inch) of the suture of Example 11 as compared to that of Comparison Example 10.

EXAMPLES 13-15

The following suture braids were fabricated in accordance with the present invention:

| Example | Overall Suture Denier | Suture Size | Pick Count | Number of Sheath Yarns | Denier of Individual Filaments | Denier of Core |
| --- | --- | --- | --- | --- | --- | --- |
| 13 | 1442 | 0 | 70 | 28 | 2.0* | 882 |
| 14 | 1621 | 0 | 70 | 28 | 1.2 | 882 |
| 15 | 1554 | 0 | 78 | 28 | 1.2 | 882 |

*Denier of sheath filaments; core filaments were 1.2 dpf.

The suture braids were coated to improve suture lubricity and knot tie-down characteristics and compared for physical properties for diameter USP knot-pull and suture tissue drag with the coated commercial suture of Comparison Example 10.

In this tissue drag test, sutures were needled with identical tapered needles to normalize any effect of needle diameter on the test.

Sutures were passed through live animal abdominal fascia tissue. The results of the tissue drag study are shown in Table IV as follows:

TABLE IV

| Example | Tissue Drag Results | | |
|---|---|---|---|
| | Diameter (min) | Knot-Pull (Kg) | Tissue Drag (gms force, maximum) |
| Comparison Example 10 | 0.419 | 4.72 | 257 |
| 13 | 0.413 | 5.27 | 35 |
| 14 | 0.428 | 5.35 | 56 |
| 15 | 0.444 | 5.04 | 50 |

Figure 5:
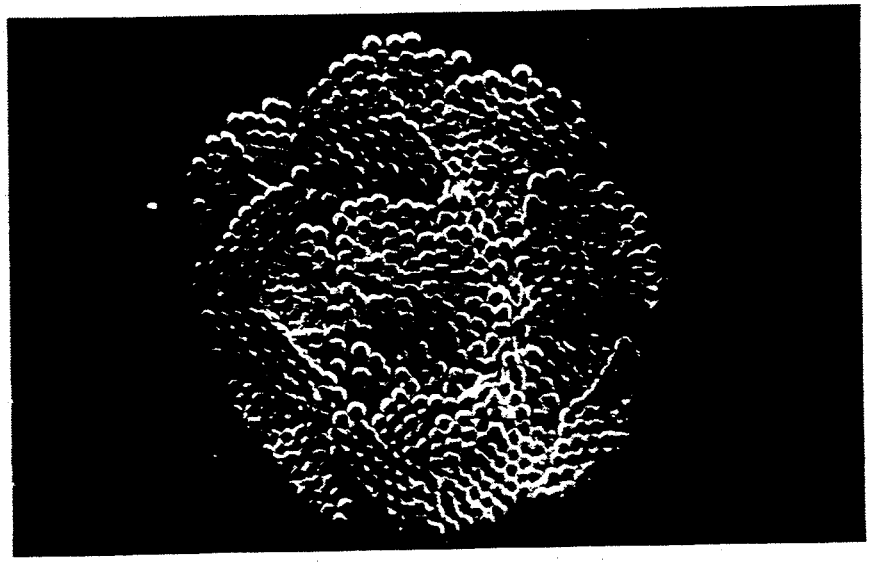
Figure 6:
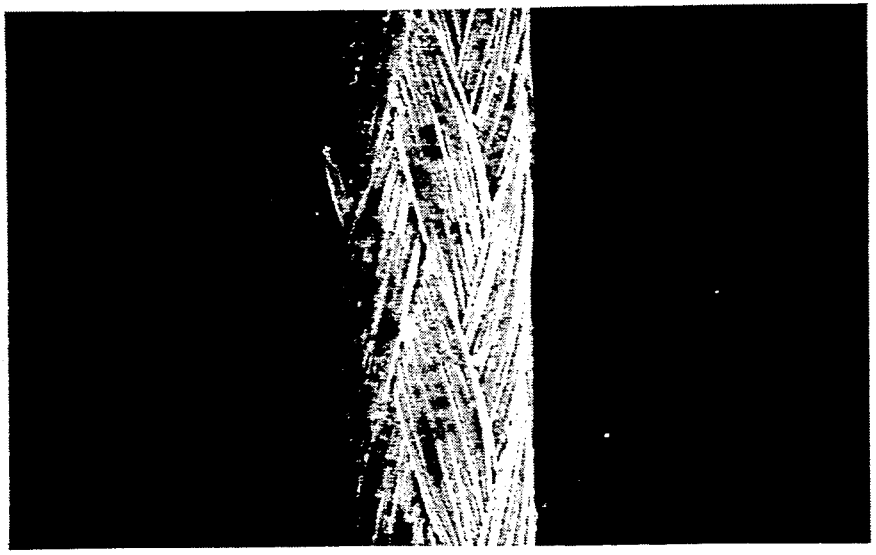
Figure 7:
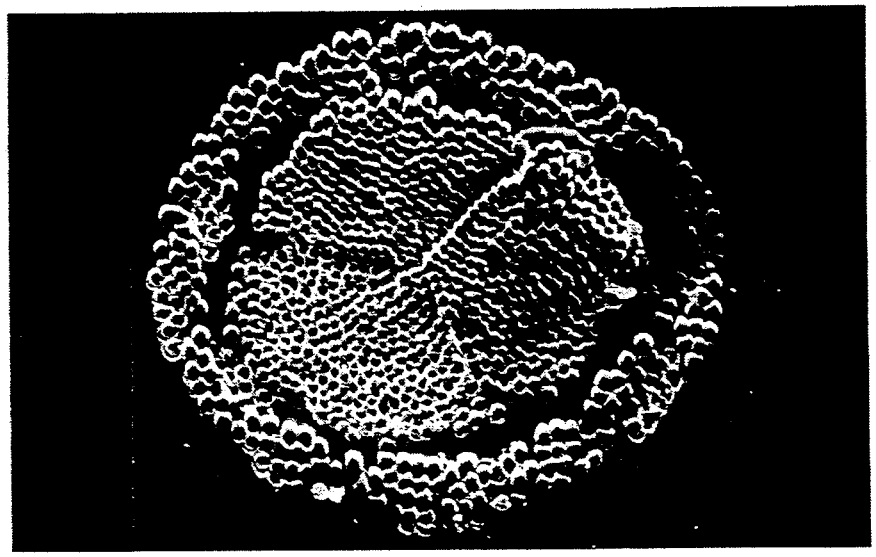
Figure 8:
Figure 9:
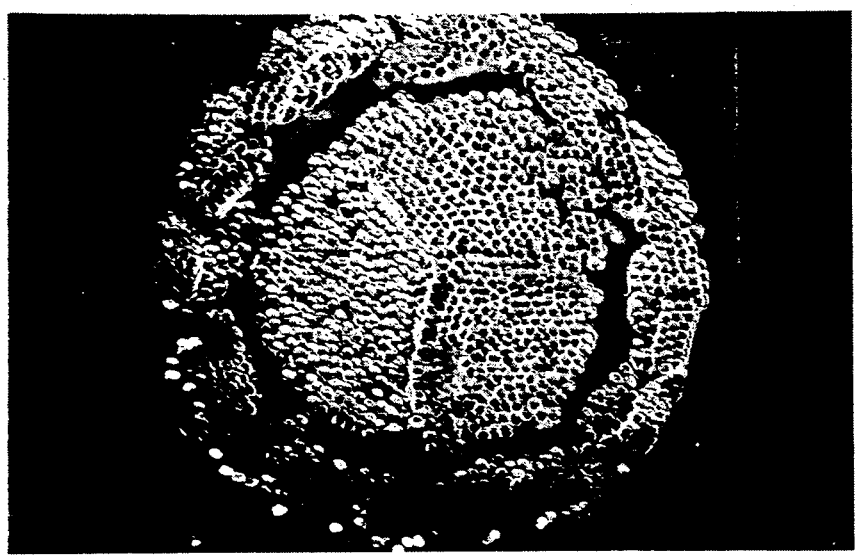
Figure 10:

These data clearly show that the smoother surface of the braided sutures fabricated in accordance with this invention provide smoother, more resistance-free passage of the suture through tissue thereby resulting in lower tissue drag and chatter. High drag forces make it more difficult for the surgeon to align tissue neatly and increase the time to complete the closure. A visual comparison of the suture of Comparative Example 10 and those of Examples 13 and 14 of this invention are consistent with the tissue drag observations set forth above. Thus, it is evident from a visual comparison of the SEM photomicrographs of FIGS. 5 and 6 (suture of Comparison Example 10 shown in cross-sectional view at 150× and linear view at 70×, respectively) with those of FIGS. 7 and 8 (suture of Example 13 shown in cross-section at 150× and linear view at 70×, respectively) and FIGS. 9 and 10 (suture of Example 14 shown in cross-section at 150× and linear view at 70×, respectively) that the external surfaces of the sutures of the present invention, i.e., those of Examples 13 and 14, are perceptibly smoother than the surfaces of the suture of Comparison Example 10.

What is claimed is:

1. A braided suture of improved construction wherein for a given range of overall suture denier, the range of pick count, number of sheath yarns and denier of individual filaments comprising a sheath yarn are related to each other as follows:

| Overall Suture Denier | Pick Count | Number of Sheath Yarns | Denier of Individual Filaments |
|---|---|---|---|
| from about 50 to about 125 | from about 50 to about 100 | from about 4 to about 16 | from about 0.2 to about 1.8 |
| greater than about 125 to about 200 | from about 50 to about 100 | from about 4 to about 16 | from about 0.2 to about 1.8 |
| greater than about 200 to about 300 | from about 50 to about 100 | from about 4 to about 16 | from about 0.2 to about 1.8 |
| greater than about 300 to about 500 | from about 50 to about 100 | from about 10 to about 20 | from about 0.2 to about 1.8 |
| greater than about 500 to about 800 | from about 50 to about 100 | from about 14 to about 20 | from about 0.2 to about 1.8 |
| greater than about 800 to about 1200 | from about 50 to about 100 | from about 16 to about 32 | from about 0.2 to about 1.8 |
| greater than about 1200 to about 2000 | from about 50 to about 100 | from about 20 to about 36 | from about 0.2 to about 1.8 |
| greater than about 2000 to about 4000. | from about 50 to about 100 | from about 20 to about 36 | from about 0.2 to about 1.8 |

2. The braided suture of claim 1 wherein for a given overall suture denier, the range of pick count, number of sheath yarns and denier of individual filaments comprising a sheath yarn are related to each other as follows:

| Overall Suture Denier | Pick Count | Number of Sheath Yarns | Denier of Individual Filaments |
|---|---|---|---|
| from about 50 to about 125 | from about 55 to about 80 | from about 6 to about 14 | from about 0.8 to about 1.4 |
| greater than about 125 to about 200 | from about 55 to about 80 | from about 6 to about 14 | from about 0.8 to about 1.4 |
| greater than about 200 to about 300 | from about 55 to about 80 | from about 6 to about 14 | from about 0.8 to about 1.4 |
| greater than about 300 to about 500 | from about 55 to about 80 | from about 12 to about 14 | from about 0.8 to about 1.4 |
| greater than about 500 to about 800 | from about 55 to about 80 | from about 14 to about 18 | from about 0.8 to about 1.4 |
| greater than about 800 to about 1200 | from about 55 to about 80 | from about 20 to about 30 | from about 0.8 to about 1.4 |
| greater than about 1200 to about 2000 | from about 55 to about 80 | from about 24 to about 34 | from about 0.8 to about 1.4 |
| greater than about 2000 to about 4000. | from about 55 to about 80 | from about 24 to about 34 | from about 0.8 to about 1.4 |

3. The braided suture of claim 2 possessing a core.

4. The braided suture of claim 3 wherein the individual filaments are fabricated from a bio-absorbable polymer.

5. The braided suture of claim 4 wherein the individual filaments are fabricated in whole or in part from a polymer derived at least in part from one or more monomers selected from the group consisting of glycolic acid, glycolide, lactic acid and lactide.

6. The braided suture of claim 2 wherein the individual filaments are fabricated from a bio-absorbable polymer.

7. The braided suture of claim 6 wherein the individual filaments are fabricated from a polymer derived at least in part from one or more monomers selected from the group consisting of glycolic acid, glycolide, lactic acid and lactide.

8. The braided suture of claim 1 possessing a core.

9. The braided suture of claim 8 wherein the overall suture denier and core denier are related to each other as follows:

| Overall Suture Denier | Denier of Core |
|---|---|
| greater than about 125 to about 200 | from about 20 to about 80 |
| greater than about 200 to about 300 | from about 30 to about 100 |

-continued

| Overall Suture Denier | Denier of Core |
| --- | --- |
| greater than about 300 to about 500 | from about 80 to about 150 |
| greater than about 500 to about 800 | from about 150 to about 300 |
| greater than about 800 to about 1200 | from about 250 to about 700 |
| greater than about 1200 to about 2000 | from about 400 to about 1200 |
| greater than about 2000 to about 4000. | from about 800 to about 2400 |

10. The braided suture of claim 9 wherein the overall suture denier and core denier are related to each other as follows:

| Overall Suture Denier | Denier of Core |
| --- | --- |
| greater than about 125 to about 200 | from about 25 to about 50 |
| greater than about 200 to about 300 | from about 50 to about 80 |
| greater than about 300 to about 500 | from about 80 to about 120 |
| greater than about 500 to about 800 | from about 180 to about 280 |
| greater than about 800 to about 1200 | from about 350 to about 650 |
| greater than about 1200 to about 2000 | from about 500 to about 1000 |
| greater than about 2000 to about 4000. | from about 1000 to about 2200 |

11. The braided suture of claim 10 wherein the individual filaments are fabricated from a bio-absorbable polymer.

12. The braided suture of claim 11 wherein the individual filaments are fabricated from a polymer derived at least in part from one or more monomers selected from the group consisting of glycolic acid, glycolide, lactic acid and lactide.

13. The braided suture of claim 9 wherein the individual filaments are fabricated from a bio-absorbable polymer.

14. The braided suture of claim 13 wherein the individual filaments are fabricated from a polymer derived at least in part from one or more monomers selected from the group consisting of glycolic acid, glycolide, lactic acid and lactide.

15. The braided suture of claim 8 wherein the individual filaments are fabricated from a bio-absorbable polymer.

16. The braided suture of claim 15 wherein the individual filaments are fabricated from a polymer derived at least in part from one or more monomers selected from the group consisting of glycolic acid, glycolide, lactic acid and lactide.

17. The braided suture of claim 1 wherein the individual filaments are fabricated from a non-absorbable material.

18. The braided suture of claim 17 wherein the non-absorbable material is cotton, silk, polyamide or polyolefin.

19. The braided suture of claim 1 wherein the individual filaments are fabricated from a bio-absorbable polymer.

20. The braided suture of claim 19 wherein the individual filaments are fabricated from a polymer derived at least in part from one or more monomers selected from the group consisting of glycolic acid, glycolide, lactic acid and lactide.

21. The braided suture of claim 1 surface coated with a composition enhancing one or more functional properties of the suture.

22. The braided suture of claim 1 containing at least one medico-surgically useful substance.

23. The braided suture of claim 1 containing at least one growth factor.

24. The braided suture of claim 1 containing at least one growth factor selected from the group consisting of fibroblast growth factor, bone growth factor, epidermal growth factor, platelet derived growth factor, macrophage derived growth factor, alveolar derived growth factor, monocyte derived growth factor and magainin.

25. A braided suture of improved construction wherein for a given range of overall suture denier, the range of pick count, number of sheath yarns and denier of individual filaments comprising a sheath yarn are related to each other as follows:

| Overall Suture Denier | Pick Count | Number of Sheath Yarns | Denier of Individual Filaments |
| --- | --- | --- | --- |
| greater than about 300 to about 500 | from about 50 to about 100 | from about 10 to about 20 | from about 0.2 to about 6.0 |
| greater than about 500 to about 800 | from about 50 to about 100 | from about 14 to about 20 | from about 0.2 to about 6.0 |
| greater than about 800 to about 1200 | from about 50 to about 100 | from about 16 to about 32 | from about 0.2 to about 6.0 |
| greater than about 1200 to about 2000 | from about 50 to about 100 | from about 20 to about 36 | from about 0.2 to about 6.0 |
| greater than about 2000 to about 4000. | from about 50 to about 100 | from about 20 to about 36 | from about 0.2 to about 6.0 |

26. The braided suture of claim 25 wherein for a given overall suture denier, the range of pick count, number of sheath yarns and denier of individual filaments comprising a sheath yarn are related to each other as follows:

| Overall Suture Denier | Pick Count | Number of Sheath Yarns | Denier of Individual Filaments |
| --- | --- | --- | --- |
| greater than about 300 to about 500 | from about 55 to about 80 | from about 12 to about 14 | from about 0.8 to about 3.0 |
| greater than about 500 to about 800 | from about 55 to about 80 | from about 14 to about 18 | from about 0.8 to about 3.0 |
| greater than about 800 to about 1200 | from about 55 to about 80 | from about 20 to about 30 | from about 0.8 to about 3.0 |
| greater than about 1200 to about 2000 | from about 55 to about 80 | from about 24 to about 34 | from about 0.8 to about 3.0 |

27. The braided suture of claim 26 possessing a core.

28. The braided suture of claim 27 wherein the individual filaments are fabricated from a bio-absorbable polymer.

29. The braided suture of claim 28 wherein the individual filaments are fabricated in whole or in part from a polymer derived at least in part from one or more monomers selected from the group consisting of glycolic acid, glycolide, lactic acid and lactide.

30. The braided suture of claim 26 wherein the individual filaments are fabricated from a bio-absorbable polymer.

31. The braided suture of claim 30 wherein the individual filaments are fabricated from a polymer derived at least in part from one or more monomers selected from the group consisting of glycolic acid, glycolide, lactic acid and lactide.

32. The braided suture of claim 25 possessing a core.

33. The braided suture of claim 25 wherein the overall suture denier and core denier are related to each other as follows:

| Overall Suture Denier | Denier of Core |
| --- | --- |
| greater than about 300 to about 500 | from about 80 to about 150 |
| greater than about 500 to about 800 | from about 150 to about 300 |
| greater than about 800 to about 1200 | from about 250 to about 700 |
| greater than about 1200 to about 2000 | from about 400 to about 1200 |
| greater than about 2000 to about 4000. | from about 800 to about 2400 |

34. The braided suture of claim 27 wherein the overall suture denier and core denier are related to each other as follows:

| Overall Suture Denier | Denier of Core |
| --- | --- |
| greater than about 300 to about 500 | from about 80 to about 120 |
| greater than about 500 to about 800 | from about 180 to about 280 |
| greater than about 800 to about 1200 | from about 350 to about 650 |
| reater than about 1200 to about 2000 | from about 500 to about 1000 |
| greater than about 2000 to about 4000. | from about 1000 to about 2200 |

35. The braided suture of claim 34 wherein the individual filaments are fabricated from a bio-absorbable polymer.

36. The braided suture of claim 35 wherein the individual filaments are fabricated from a polymer derived at least in part from one or more monomers selected from the group consisting of glycolic acid, glycolide, lactic acid and lactide.

37. The braided suture of claim 32 wherein the individual filaments are fabricated from a bio-absorbable polymer.

38. The braided suture of claim 37 wherein the individual filaments are fabricated from a polymer derived at least in part from one or more monomers selected from the group consisting of glycolic acid, glycolide, lactic acid and lactide.

39. The braided suture of claim 33 wherein the individual filaments are fabricated from a bio-absorbable polymer.

40. The braided suture of claim 39 wherein the individual filaments are fabricated from a polymer derived at least in part from one or more monomers selected from the group consisting of glycolic acid, glycolide, lactic acid and lactide.

41. The braided suture of claim 25 wherein the individual filaments are fabricated from a non-absorbable material.

42. The braided suture of claim 41 wherein the non-absorbable material is cotton, silk, polyamide or polyolefin.

43. The braided suture of claim 25 wherein the individual filaments are fabricated from a bio-absorbable polymer.

44. The braided suture of claim 43 wherein the individual filaments are fabricated from a polymer derived at least in part from one or more monomers selected from the group consisting of glycolic acid, glycolide, lactic acid and lactide.

45. The braided suture of claim 25 surface coated with a composition enhancing one or more functional properties of the suture.

46. The braided suture of claim 25 containing at least one medico-surgically useful substance.

47. The braided suture of claim 25 containing at least one growth factor.

48. The braided suture of claim 25 containing at least one growth factor selected from the group consisting of fibroblast growth factor, bone growth factor, epidermal growth factor, platelet derived growth factor, macrophage derived growth factor, alveolar derived growth factor, monocyte derived growth factor and magainin.

* * * * *